(12) United States Patent
Viebach et al.

(10) Patent No.: US 11,612,304 B2
(45) Date of Patent: Mar. 28, 2023

(54) ENDOSCOPE HAVING A WIDE-ANGLE LENS AND A WORKING CHANNEL

(71) Applicant: HOYA CORPORATION, Tokyo (JP)

(72) Inventors: Thomas Viebach, Friedberg (DE); Tilman Schroeter, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 55 days.

(21) Appl. No.: 16/494,926

(22) PCT Filed: Mar. 28, 2018

(86) PCT No.: PCT/IB2018/000308
§ 371 (c)(1),
(2) Date: Sep. 17, 2019

(87) PCT Pub. No.: WO2018/185549
PCT Pub. Date: Oct. 11, 2018

(65) Prior Publication Data
US 2020/0008659 A1    Jan. 9, 2020

(30) Foreign Application Priority Data

Apr. 3, 2017 (DE) ...................... 10 2017 107 106.7

(51) Int. Cl.
*A61B 1/00* (2006.01)
*A61B 1/05* (2006.01)
(Continued)

(52) U.S. Cl.
CPC ...... *A61B 1/00096* (2013.01); *A61B 1/00091* (2013.01); *A61B 1/00098* (2013.01);
(Continued)

(58) Field of Classification Search
CPC ............ A61B 1/00174; A61B 1/00183; A61B 1/00181; A61B 1/012; A61B 1/015;
(Continued)

(56) References Cited

U.S. PATENT DOCUMENTS 7,883,459 B2   2/2011  Miyagi et al.
8,094,354 B2   1/2012  Murayama
(Continued)

FOREIGN PATENT DOCUMENTS

CN   101426414   5/2009
CN   102370453   3/2012
(Continued)

OTHER PUBLICATIONS

Japanese Office Action, Japanese Patent Office, Application No. 2019-537165, dated Sep. 1, 2020.
(Continued)

*Primary Examiner* — Ryan N Henderson
*Assistant Examiner* — Pamela F Wu
(74) *Attorney, Agent, or Firm* — Greenblum & Bernstein, P.L.C.

(57) ABSTRACT

The invention relates to an endoscope including an endoscope head, a wide-angle lens on the distal end of the endoscope head, and a working channel extending in the endoscope head. Proximally from the wide-angle lens, the working channel is bent laterally toward the outer circumference of the endoscope head, wherein a distal working channel opening is formed on a lateral side of the endoscope head.

22 Claims, 9 Drawing Sheets

(51) Int. Cl.
*A61B 1/06* (2006.01)
*A61B 1/31* (2006.01)

(52) U.S. Cl.
CPC ............ *A61B 1/00174* (2013.01); *A61B 1/05* (2013.01); *A61B 1/0684* (2013.01); *A61B 1/0692* (2013.01); *A61B 1/06* (2013.01); *A61B 1/31* (2013.01)

(58) Field of Classification Search
CPC ... A61B 1/018; A61B 1/0008; A61B 1/00096; A61B 1/00098; A61B 1/0684; A61B 1/0692; A61B 1/31; A61B 1/0676; A61B 1/05; A61B 1/00101; A61B 1/00091; A61B 1/051; A61B 1/04; A61B 1/00163; A61B 1/0661; A61B 1/0607
USPC .................. 600/104, 109, 129–130, 153
See application file for complete search history.

(56) References Cited

U.S. PATENT DOCUMENTS

| | | | |
|---|---|---|---|
| 8,164,839 B2 | 4/2012 | Nasu | |
| 8,277,373 B2* | 10/2012 | Maahs | A61B 1/0008 600/107 |
| 8,360,964 B2* | 1/2013 | Ertas | A61B 1/0005 600/166 |
| 8,425,406 B2* | 4/2013 | Smith | A61B 1/00098 600/114 |
| 8,928,746 B1 | 1/2015 | Stevrin et al. | |
| 9,140,888 B2 | 9/2015 | Fujii | |
| 10,036,883 B2 | 7/2018 | Fujii | |
| 2006/0069314 A1* | 3/2006 | Farr | A61B 1/00096 600/179 |
| 2007/0118013 A1 | 5/2007 | Miyagi et al. | |
| 2007/0197875 A1* | 8/2007 | Osaka | A61B 1/04 600/173 |
| 2008/0051629 A1* | 2/2008 | Sugiyama | A61B 1/018 600/114 |
| 2008/0242935 A1* | 10/2008 | Inoue | A61B 1/07 600/176 |
| 2009/0048490 A1 | 2/2009 | Iijima | |
| 2009/0069633 A1 | 3/2009 | Orihara et al. | |
| 2009/0147076 A1* | 6/2009 | Ertas | H04N 5/2254 348/E7.085 |
| 2010/0010301 A1 | 1/2010 | Hale et al. | |
| 2011/0065985 A1* | 3/2011 | Wehrheim | A61B 1/00149 600/106 |
| 2011/0157574 A1* | 6/2011 | Kato | A61B 1/05 355/71 |
| 2011/0160530 A1* | 6/2011 | Ratnakar | A61B 1/00105 600/104 |
| 2012/0016202 A1* | 1/2012 | Baum | A61B 1/05 600/182 |
| 2012/0232340 A1 | 9/2012 | Levy et al. | |
| 2013/0237755 A1 | 9/2013 | Singh | |
| 2014/0107415 A1* | 4/2014 | Amling | A61B 1/00078 600/109 |
| 2015/0196190 A1 | 7/2015 | Levy et al. | |
| 2016/0100750 A1* | 4/2016 | Furuta | G02B 23/2423 362/558 |
| 2016/0220103 A1 | 8/2016 | Kennedy, II et al. | |
| 2017/0023787 A1 | 1/2017 | Kirma et al. | |
| 2017/0119435 A1* | 5/2017 | Gross | A61B 1/05 |
| 2017/0127915 A1 | 5/2017 | Viebach et al. | |
| 2017/0280974 A1 | 10/2017 | Levy et al. | |
| 2017/0303774 A1 | 10/2017 | Nasu | |
| 2018/0168431 A1 | 6/2018 | Kang et al. | |
| 2019/0053695 A1 | 2/2019 | Fujii et al. | |
| 2019/0350449 A1 | 11/2019 | Tajima et al. | |

FOREIGN PATENT DOCUMENTS

| | | |
|---|---|---|
| CN | 104434001 | 3/2015 |
| CN | 105142490 | 12/2015 |
| CN | 106061350 | 10/2016 |
| CN | 205795635 | 12/2016 |
| DE | 112004001398 T5 | 6/2006 |
| DE | 102010013413 A1 | 6/2011 |
| EP | 1774895 | 4/2007 |
| EP | 1891885 | 2/2008 |
| EP | 2033570 | 3/2009 |
| JP | 11-267088 | 10/1999 |
| JP | H11-267088 A | 10/1999 |
| JP | 2001-95756 | 4/2001 |
| JP | 2005-80713 | 3/2005 |
| JP | 2006-34543 A | 2/2006 |
| JP | 2009-60925 | 3/2009 |
| JP | 2009-153641 A | 7/2009 |
| JP | 2010-17552 A | 1/2010 |
| JP | 2013-99426 A | 5/2013 |
| WO | 2015/056106 | 4/2015 |
| WO | 2017/026653 | 2/2017 |

OTHER PUBLICATIONS

Chinese Office Action, Chinese Patent Office, Application No. 201880015741.3, dated Mar. 31, 2021, with machine English translation.
Chinese Search Report, Chinese Patent Office, Application No. 201880015741.3, dated Mar. 31, 2021, with machine English translation.
Official Communication issued in International Bureau of WIPO Patent Application No. PCT/IB2018/000308, dated May 24, 2018 (with English translation).
Chinese Office Action, Chinese Patent Office, Application No. 201880015741.3, dated Oct. 26, 2021, with machine English translation.
Chinese Office Action, Chinese Patent Office, Application No. 201880015741.3, dated Mar. 28, 2022, with machine English translation.
Office Action issued in German Counterpart Patent Appl. No. 102017107106.7, dated Jan. 4, 2018.
Office Action issued in German Counterpart Patent Appl. No. 102017107106.7, dated Jul. 2, 2018.

* cited by examiner

ENDOSCOPE HAVING A WIDE-ANGLE LENS AND A WORKING CHANNEL

The present invention relates to an endoscope. More precisely, the invention relates to an endoscope comprising an endoscope head having a wide-angle lens on the distal end of the endoscope head and a working channel for guiding micro tools.

The working area of an endoscope is, at the distal end of the endoscope head, equipped with a camera, an illumination means such as, for example, an LED, and a working channel. The working area is to be well illuminated and easy to view. The working area is the area in which a micro tool advanced inside the working channel is moved further or is employed on the patient.

To achieve a good illumination, a large number of LEDs can be arranged on the distal end of the endoscope head.

It is the object of the present invention to provide an improved endoscope, in which an image of the working area can be captured in an advantageous manner.

This object is achieved by an endoscope comprising the features of claim 1.

Advantageous further developments are subject matter of the dependent claims.

In the invention, an endoscope comprises an endoscope head, a wide-angle lens on the distal end of the endoscope head, and a working channel extending in the endoscope head. Proximally from the wide-angle lens, the working channel is bent laterally toward the outer circumference of the endoscope head, wherein a distal working channel opening is formed on a lateral side of the endoscope head.

This endoscope comprises a wide-angle lens on the distal end of the endoscope head. Such a wide-angle lens can be a super wide-angle lens having an optical viewing angle of more than 180 degrees. Such a wide-angle lens can be a so-called fisheye lens. This wide-angle lens can be of such a size that it takes up the entire distal front region on the distal end of the endoscope head. Thus, a very large viewing angle of the captured area is possible. Extending the field of view to the super wide angle range (fisheye>180°) makes it possible to detect suspicious tissue structures in previously hidden regions of the large intestine (e.g. even behind intestinal folds).

For reasons of space, the working channel does not extend in a straight manner to the distal end of the endoscope head, but is, proximally from the wide-angle lens, bent laterally toward the outer circumference of the endoscope head, such that a distal working channel opening is formed on a lateral side of the endoscope head.

Hence, an endoscope can be provided, which enables a very large viewing angle in the captured area and whose overall dimensions are kept small since the diameter of the distal end of the endoscope (the endoscope head) does not have to be designed unnecessarily large. The distal end would have to be designed significantly larger, for example, if the working channel opening was arranged laterally from the wide-angle lens and in parallel to the optical axis.

Such an endoscope can advantageously be used as colonoscope. Especially in colonoscopy a large field of view is beneficial.

Adjacent to the wide-angle lens, an illumination means can be arranged on the distal end of the endoscope head, wherein the distal working channel opening opens proximally from the illumination means. Thus, the image to be captured by the wide-angle lens can be well illuminated. Although the distal working channel opening is located proximally from the illumination means, it is directed in the distal direction.

Alternatively, adjacent to the wide-angle lens, an illumination means can be arranged on the distal end of the endoscope head, wherein the distal working channel opening opens in the region of the illumination means. In this alternative, the distal working channel opening is further offset in the distal direction and can be surrounded by the illumination means. Thus, the image to be captured by the wide-angle lens can still be well illuminated by the illumination means.

As a further alternative, adjacent to the wide-angle lens, an illumination means can be arranged on the distal end of the endoscope head, wherein the distal working channel opening opens in the region of the wide-angle lens. Thus, the distal working channel opening protrudes into the surface of the wide-angle lens. The distal working channel opening can even be surrounded by parts of the surface of the wide-angle lens.

The illumination means can surround the distal end region of the wide-angle lens in an annular manner or as a ring portion. The illumination means can be designed in an annular manner when it is not interrupted by the distal working channel opening. The illumination means can be designed as a ring portion when it is interrupted by the distal working channel opening.

Adjacent to the wide-angle lens, a spray means for lens cleaning can be arranged on the distal end of the endoscope head, wherein the distal working channel opening opens proximally from the spray means. The spray means can advantageously clean the distal surface of the wide-angle lens.

On the distal end of the endoscope head, the wide-angle lens can be completely or partially surrounded by a transparently designed region of the endoscope head. On the distal end of the endoscope head, the wide-angle lens can be completely surrounded by the transparently designed region of the endoscope head when the transparently designed region is not interrupted by the distal working channel opening. On the distal end of the endoscope head, the wide-angle lens can be partially surrounded by the transparently designed region of the endoscope head when the transparently designed region is interrupted by the distal working channel opening.

The transparently designed region of the endoscope head can form a transition from the distal to the lateral side of the endoscope head.

The working channel can include a proximal working channel portion and a distal working channel end portion, wherein the proximal working channel portion extends in parallel to the longitudinal axis of the endoscope, and the distal working channel end portion is gently bent in the distal direction from the proximal working channel portion toward the distal working channel opening in a sloping manner.

The distal working channel end portion can extend in the distal direction at an acute angle to the central axis of the endoscope head.

The distal working channel end portion can abut, at least in one portion thereof, on the wide-angle lens.

At least one portion of the distal working channel end portion can extend into the form (material) of the wide-angle lens.

An opening of a water spray nozzle can be provided adjacent to the distal working channel opening.

Proximally from the wide-angle lens, the distal working channel opening can adjoin the wide-angle lens.

On the lateral side of the endoscope head, the distal working channel opening can extend into the form of the wide-angle lens.

Combinations of the design are possible, of course. For example, the distal working channel end portion can, at least in one portion thereof, abut on the wide-angle lens, and the distal working channel opening can be slightly spaced apart from the wide-angle lens. Further, the distal working channel end portion can, at least in one portion thereof, abut on the wide-angle lens, and the distal working channel opening can adjoin the wide-angle lens. Moreover, the distal working channel end portion can, at least in one portion thereof, abut on the wide-angle lens, and the distal working channel opening can extend into the form of the wide-angle lens or open in such a manner that it is surrounded by the surface of the wide-angle lens. These variants of the arrangement of the distal working channel opening are also applicable to the other design options of the distal working channel end portion. Thus, this results in respective different angles or different bendings of the distal working channel end portion relative to the extension of the endoscope head.

An image section of the wide-angle lens, which is almost parallel to the distal course of the end of the working channel, can be selectable. The wide-angle lens delivers an overall image of the viewed scene. This overall image is very large. A section which will be analyzed in further detail can be selected from this overall image. For example, the section in which an instrument advanced through the working channel becomes active, i.e. an image section located laterally from the endoscope head, can be used as such a selected section of the overall image.

Initially, the wide-angle lens delivers distorted image sections. The selected image section can be digitally equalized by means of image processing.

Thus, the digitally equalized image section can be selected from the overall image such that the instrument emerges in a manner apparently directed towards the center of the image. Thus, the working direction of the endoscope is diagonally lateral, while the user's view on the working area remains familiarly central.

The viewing angle of the wide angle lens can be larger than 180°, wherein it can preferably be larger than 200° or even larger than 220°. An unusually large viewing angle of the wide-angle lens is possible according to the invention.

The endoscope can be a flexible endoscope.

The endoscope can be a video endoscope.

The previously described aspects of the present invention can be suitably combined.

In the following, the present invention is described in detail by means of embodiments while referring to the drawings.

FIRST EMBODIMENT

Figure 1:
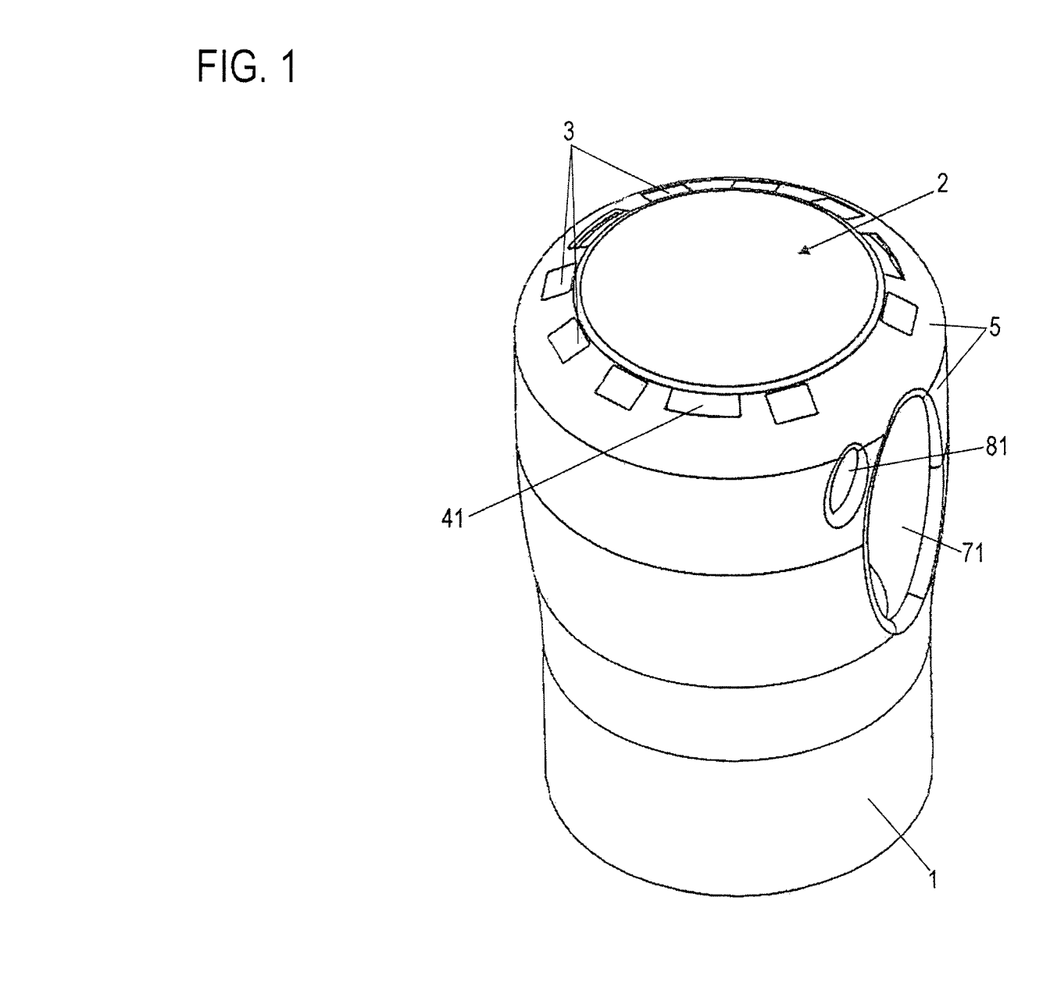
FIG. 1 shows a schematic perspective view of a distal portion of an endoscope of a first embodiment of the present invention.
Figure 2:
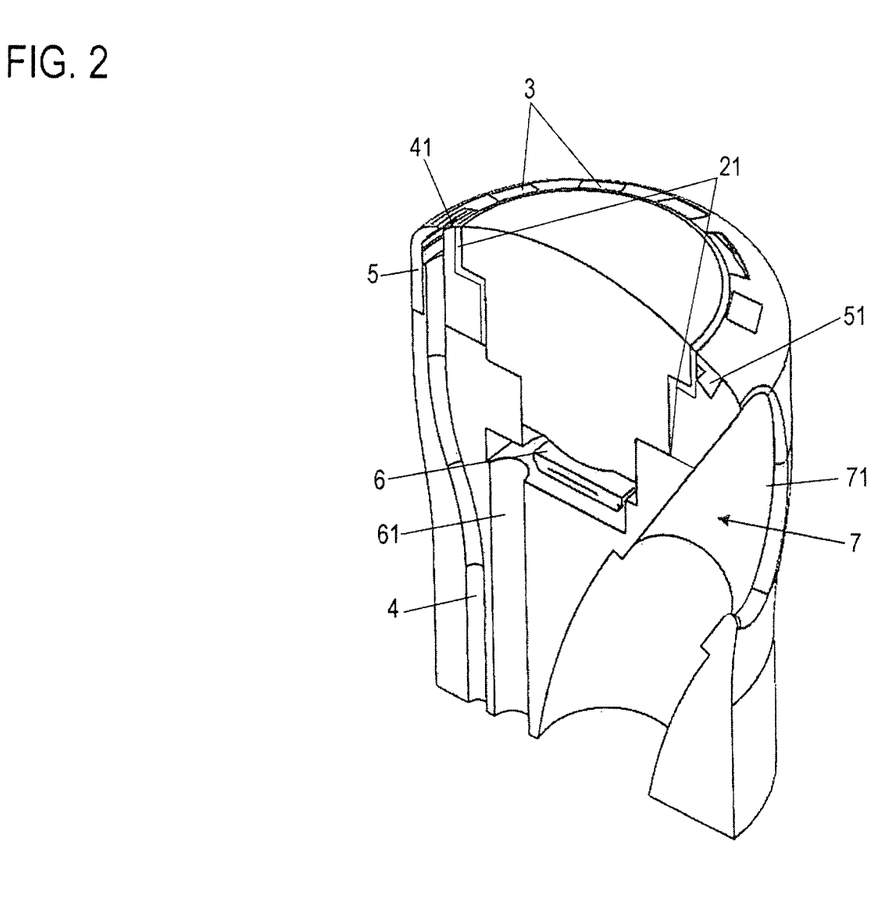
FIG. 2 shows a schematic perspective view of the endoscope of FIG. 1 in a sectional representation, the sectional plane passing through a distal working channel opening.
Figure 3:
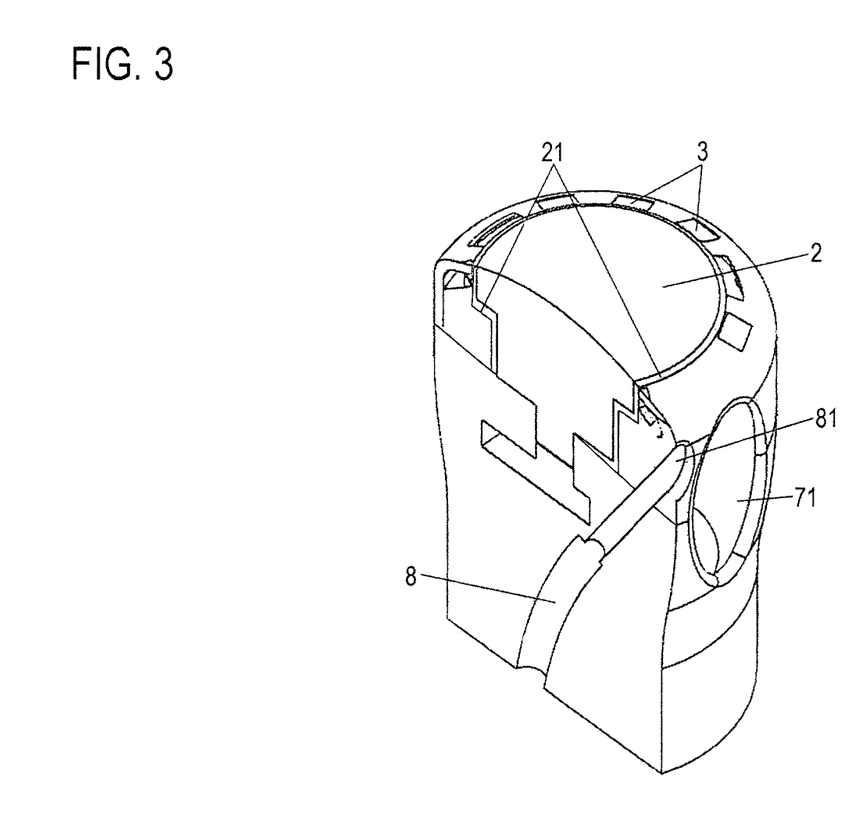
FIG. 3 shows a further schematic perspective view of the endoscope of FIG. 1 in a sectional representation, the sectional plane passing through a channel of a water spray nozzle.

Referring to FIGS. 1 to 3, a first embodiment of the present invention is described below.

FIGS. 1 and 2 both show a schematic perspective view of a distal portion of an endoscope of a first embodiment of the present invention.

In particular, an endoscope head 1 of the endoscope is shown. More precisely, a distal end piece of the endoscope head 1 is shown. The endoscope head 1 includes a wide-angle lens 2 on its distal end. The wide-angle lens 2 has a central axis corresponding to the central axis of the endoscope head 1. The distal surface (lens surface) of the wide-angle lens 2 is outwardly curved and faces in the distal direction of the endoscope. Thus, in the present embodiment, the wide-angle lens 2 is arranged concentrically with respect to the central axis of the endoscope head 1, as shown in FIG. 1. Hence, the wide-angle lens 2 is oriented in the distal direction. Alternatively, the wide-angle lens 2 can be arranged at an angle relative to the central axis of the endoscope head 1. In this alternative, the wide-angle lens 2 would be directed in the lateral direction, i.e. to the side.

The wide-angle lens 2 can be a super wide-angle lens and can have a viewing angle of more than 180 degrees in the distal direction. Thus, not only the region on the distal side of the endoscope head 1 is captured by the wide-angle lens 2, but also a region located laterally from the distal end of the endoscope head 1.

The wide-angle lens 2 can be a so-called fisheye lens.

Adjacent to the distal end surface of the wide-angle lens 2, an illumination means in the form of LEDs 3 is arranged on the distal side of the endoscope head 1. In the example of FIG. 1, the LEDs 3 are evenly distributed around the distal end surface of the wide-angle lens 2. The LEDs 3 adjoin the distal end surface of the wide-angle lens 2.

As shown in FIG. 2, a channel 4 for air/water is arranged inside of the endoscope, the channel extending from a proximal portion of the endoscope (operating part) up to a spray nozzle 41 for lens cleaning. In the invention, one single channel 4 alternatingly conducting air and/or water to the spray nozzle 41 can be applied.

Alternatively, two supply channels can be applied; a first supply channel thereof conducts water and a second supply channel conducts air. Both supply channels open into the channel 4. Thus, water or air or a water-air mixture can be sprayed by the spray nozzle 41 on the distal end of the channel 4.

The spray nozzle 41 has the purpose of cleaning the distal end surface of the wide-angle lens 2. In the example of FIG. 1, three spray nozzles 41 are provided. The spray nozzles 41 are evenly distributed around the distal end surface of the wide-angle lens 2. The spray nozzles 41 adjoin the distal end surface of the wide-angle lens 2.

The distal end surface of the wide-angle lens 2 is surrounded by a transparent cap 5. The transparent cap 5 is formed as a ring member, for example. The transparent cap 5 is made of a transparent material, such as glass or plastic, for example.

A concentric annular depression 51 is formed on the distal end surface of the transparent cap 5. The LEDs 3 and the spray nozzles 41 are arranged in the concentric annular depression 51 of the transparent cap 5. Between the LEDs 3 and the spray nozzles 41, the concentric annular depression 51 of the transparent cap 5 is filled with a transparent material.

The outside surface of the LEDs 3 can be aligned with the outside surface of the transparent material. In this design, the outside surfaces of the LEDs 3 are arranged on the distal outside surface of the endoscope head 1.

In a variation, the LEDs 3 are provided on the proximal bottom of the concentric annular depression of the transparent cap 5. Here, the outside surface of the LEDs 3 is spaced apart from the outside surface of the transparent material. In this design, the outside surfaces of the LEDs 3 are not arranged on the distal outside surface of the endoscope head 1, but covered by the transparent material.

The light of the LEDs 3 can exit through the transparent cap 5 in the distal direction as well as in the lateral direction. The scenery captured by the wide-angle lens 2 can be well illuminated through the transparent cap 5.

A foreign light protection 21 preventing the light of the LEDs 3 from entering the wide-angle lens 2 directly from the side is provided on the lateral edge of the wide-angle lens 2 between the wide-angle lens 2 and the transparent cap 5.

The wide-angle lens 2 is outwardly curved (see FIG. 2) and can thus tangentially capture image information up to the edge where the transparent material provided in the concentric annular depression of the transparent cap 5 adjoins.

Thus, together with the transparent cap 5, the wide-angle lens 2 takes up the entire distal front region on the distal end of the endoscope head 1.

On the proximal side of the wide-angle lens 2, an image sensor 6 is centrically arranged in the endoscope head 1. The image sensor 6 is used to receive the image information transmitted by the wide-angle lens 2. The received image information is transferred to the proximal portion of the endoscope (operating part) via cables in a cable channel 61.

The endoscope head 1 comprises a working channel 7. The working channel 7 accommodates micro tools for examining e.g. the intestinal wall, etc. On the distal side, the working channel 7 has a working channel outlet as distal opening 71.

The working channel 7 comprises a proximal working channel portion (not shown) and a distal working channel end portion. The proximal working channel portion (not shown) extends in parallel to the longitudinal axis of the endoscope from the proximal portion of the endoscope (operating part) up to a transition to the distal working channel end portion.

The distal working channel end portion is gently bent in the distal direction from the proximal working channel portion to the distal working channel opening 71 in a sloping manner. The distal working channel opening 71 is formed on the lateral side (circumferential side) of the endoscope head 1. Thus, the inventive endoscope includes the distal working channel opening 71 as a lateral working channel outlet.

The distal working channel opening 71 as lateral working channel outlet is arranged proximally from the wide-angle lens 2.

The distal working channel opening 71 can be proximally spaced apart from the wide-angle lens 2. Alternatively, the distal working channel opening 71 can proximally adjoin the wide-angle lens 2.

In a preferred design, a circumferential portion of the distal working channel end portion protrudes into the form of the transparent cap 5, as shown in FIGS. 1 and 2.

In a further alternative, a circumferential portion of the distal working channel end portion can protrude into the form of the wide-angle lens 2 without a part of the transparent cap 5 being provided between the working channel 7 and the wide-angle lens 2.

Regardless of the course of the distal working channel end portion, the distal working channel opening 71 can protrude into the transparent cap 5. In FIGS. 1 and 2, a circumferential portion of the distal working channel opening 71 protrudes into the form of the transparent cap 5.

In a further alternative, a circumferential portion of the distal working channel opening 71 can protrude into the form of the wide-angle lens 2 without a part of the transparent cap 5 being provided between the working channel opening 71 and the wide-angle lens 2. In this alternative, at least one portion of the distal working channel opening 71 is provided on the annular region of the LEDs 3. Thus, in this alternative, at least one portion of the distal working channel opening 71 is surrounded by LEDs 3 radially with respect to the exit point of the central axis on the distal end surface of the wide-angle lens 2.

In the embodiment, the distal working channel end portion including the distal working channel opening 71 is oriented in a direction forming an acute angle with respect to the longitudinal extension of the endoscope head 1. In other words, the distal working channel end portion extends at an acute angle with respect to the central axis of the endoscope head 1 in the distal direction.

FIG. 3 shows a sectional plane through a channel 8 of a water spray nozzle 81.

As it is shown in FIG. 3, the opening of the water spray nozzle 81 is provided adjacent to the distal working channel opening 71. The opening of the water spray nozzle 81 forms a distal end of a water supply channel 8. The water supply channel 8 extends in parallel to the working channel 7. The water spray nozzle 81 is used to supply water, if required, to a working site where an instrument guided through the working channel 7 is employed. Adjacent to the water spray nozzle 81, a distal opening of a suction channel (not shown) can be provided. The water sprayed to the working site can be sucked off again through the suction channel.

Variants and Further Embodiments

Different variants and further embodiments, each showing a different arrangement of the distal working channel opening 71, are described in the following.

Figure 4:
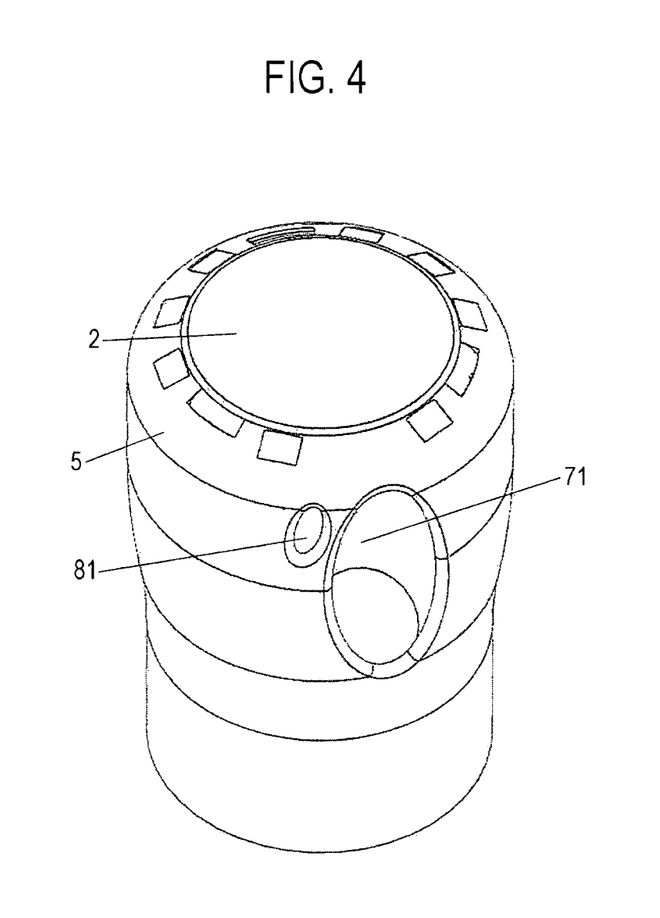
FIG. 4 shows a schematic perspective view of a distal portion of an endoscope in a variant where the distal working channel opening adjoins a transparent cap.

FIG. 4 shows a variant where the distal working channel opening 71 adjoins a transparent cap 5. The location of the water spray nozzle 81 is also selected in such a manner that the water spray nozzle 81 adjoins the transparent cap 5. Thus, the distal working channel opening 71 is provided on the endoscope laterally below (i.e. proximally from) the assembly formed by the wide-angle lens 2 and the transparent cap 5. In other words, the distal working channel opening 71 is arranged below (i.e. proximally from) the illumination means.

Figure 5:
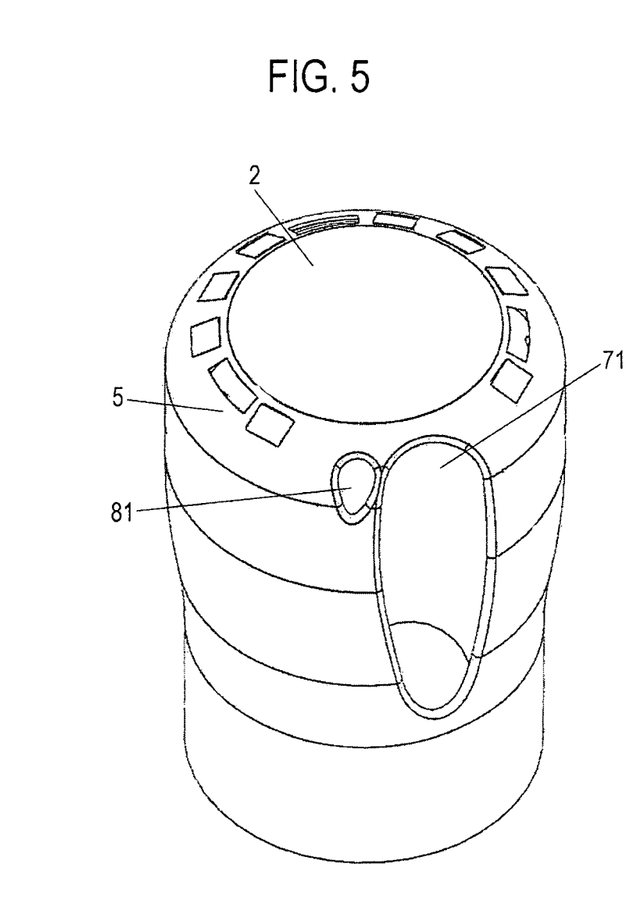
FIG. 5 shows a schematic perspective view of a distal portion of an endoscope in a variant where the distal working channel opening reaches further into the region of the transparent cap.

FIG. 5 shows a variant where the distal working channel opening 71 reaches further into the region of the transparent cap 5. The location of the water spray nozzle 81 is also selected in such a manner that the water spray nozzle 81 reaches into the region of the transparent cap 5. Here, the distal working channel opening 71 is, at least in the distal portion, surrounded by the transparent cap 5. Relative to the variant of FIG. 4, a more acute angle has been selected for the working channel outlet in FIG. 5.

Figure 6:
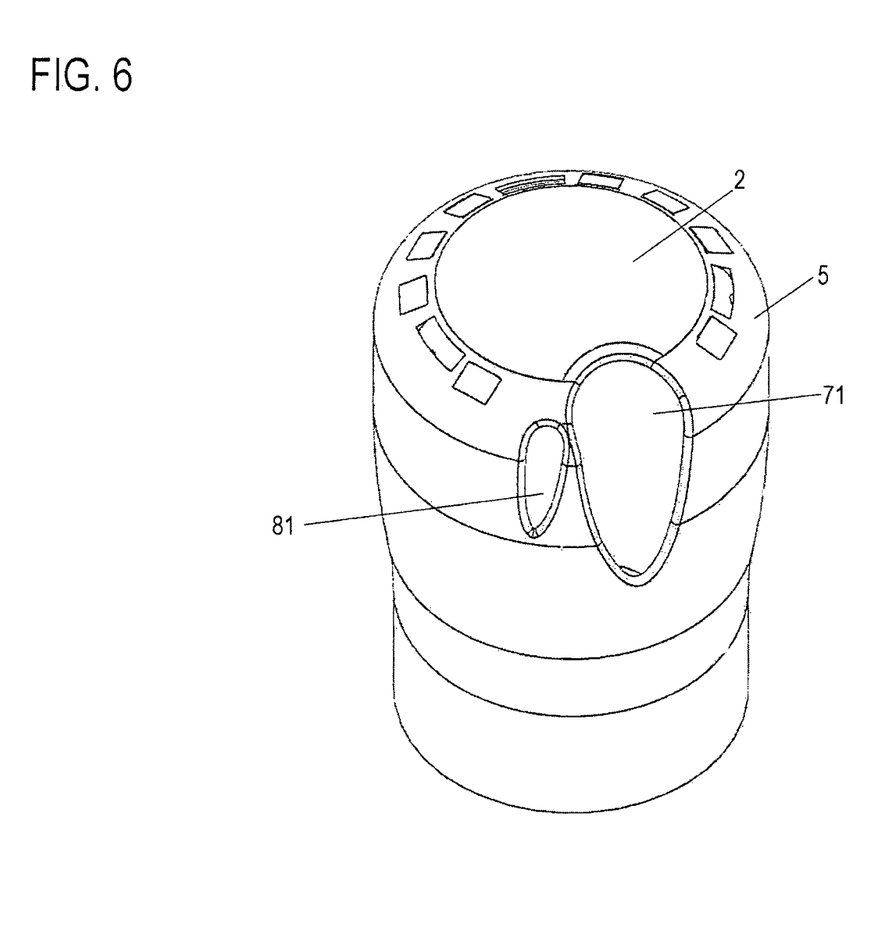
FIG. 6 shows a schematic perspective view of a distal portion of an endoscope in a variant where the distal working channel opening protrudes even slightly into the region of the wide-angle lens.

FIG. 6 shows a variant where the distal working channel opening 71 even protrudes slightly into the region of the wide-angle lens 2. The location of the water spray nozzle 81 is selected in such a manner that it reaches into the region of the transparent cap 5. Here, the distal working channel opening 71 interrupts the transparent cap 5. Relative to the variant of FIG. 5, an even more acute angle has been selected for the working channel outlet in FIG. 6.

In a variant which is not shown, the proximal portion of the distal working channel opening 71 can be located proximally from a proximal portion of the transparent cap 5.

In a further variant which is not shown, the distal working channel opening 71 can be completely located in the region of the wide-angle lens 2. In this way, an even more acute angle for the working channel outlet is realized.

The working channel outlet itself is preferably consistently curved. The working channel outlet can also have a curvature increasing towards the working channel opening 71. A curvature decreasing towards the working channel opening 71 would also be possible.

The working channel outlet does not necessarily have to be curved. Alternatively, starting from its bending having a curvature, the working channel outlet can extend in an almost straight manner from the straight course up to the working channel opening 71.

Hence, different angles and different shapes of the distal working channel outlet are possible in the invention.

Function of the Invention

In the endoscope according to the invention, the outlet 71 of the working channel 7 faces to the side.

A micro tool can be advanced inside the working channel 7 such that it is pushed to a working site through the lateral distal working channel opening 71. Here, the working site can even be located laterally from the distal end piece of the endoscope head 1.

The wide-angle lens 2 has a viewing angle of more than 180 degrees and can thus capture the working site even when it is located laterally from the distal end piece of the endoscope head 1.

In this position, when the endoscope head 1 is arranged in the intestine, for example, the intestinal wall can be well illuminated, viewed and captured. In this way, tissue abnormalities hidden in or behind bends and folds can be detected. Moreover, tissue abnormalities hidden in or behind bends and folds can be conveniently reached by micro tools.

Advantages of the Invention

The distally arranged wide-angle lens 2 enables "forward-directed" viewing (i.e. in the distal direction) upon introduction of the endoscope 1.

Since the wide-angle lens 2 is combined with the obliquely extending working channel end piece, the distal end of the working channel 7 does not affect the wide-angle lens 2.

In accordance with the invention, a wide-angle endoscope comprising a working channel and a still small diameter is provided. Through the extended perspective of the wide-angle lens 2 (e.g. the fisheye lens) tissue abnormalities previously hidden in bends and folds can be detected.

Since the wide-angle lens 2 enables a viewing angle of more than 180 degrees and the annular illumination is used, the working site where a micro tool advanced through the working channel 7 is active, can be well illuminated and captured.

This working site can even be located laterally from the distal end piece of the endoscope head 1.

Due to the construction in accordance with the invention, the distal working channel end portion including the distal working channel opening 71 is oriented in the same direction as the viewing direction of a portion of the wide-angle lens 2, which is supposed to capture the working site.

The wide-angle lens 2 can capture an image section having a viewing direction parallel to the direction of the distal working channel end portion through which a tool is pushed.

Selecting an Image Section

In the embodiment, the endoscope head 1 comprises the wide-angle lens 2 that can be formed as a so-called fisheye lens. The wide-angle lens 2 can be divided into individually selectable sectors.

Figure 7:
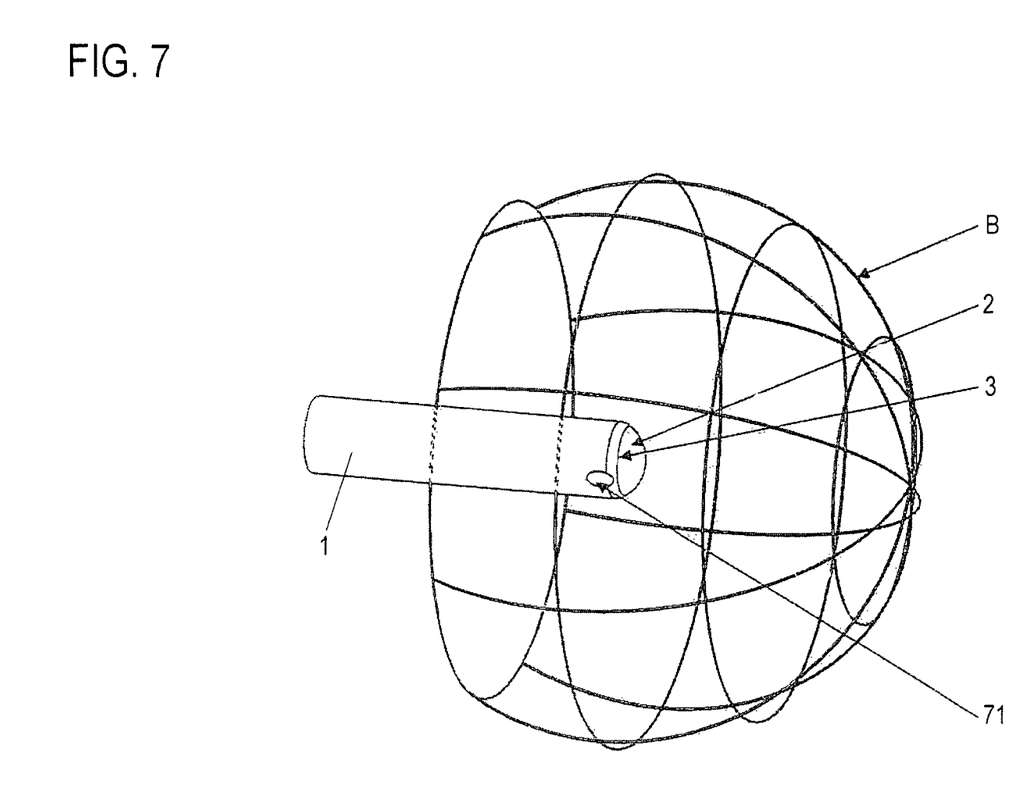
FIG. 7 shows a schematic perspective view of a distal portion of an endoscope with an indicated field of view of the wide-angle lens.

FIG. 7 schematically indicates a field of view B of the wide-angle lens 2. The wide-angle lens 2 shown here has, for example, a field of view B of 235°. Thus, a very large area, for example in a patient's intestine, can be viewed and captured. As indicated in FIG. 7, the field of view B can be gridded and divided into individual portions. These individual portions are formed as sectors. By means of image processing, a specific image portion (image section) can be selected from the many resulting individual portions. However, this is to be understood as an example. The virtual navigation in the entire field of view B of the wide-angle lens 2 is also possible in a continuously controllable manner.

Figure 8:
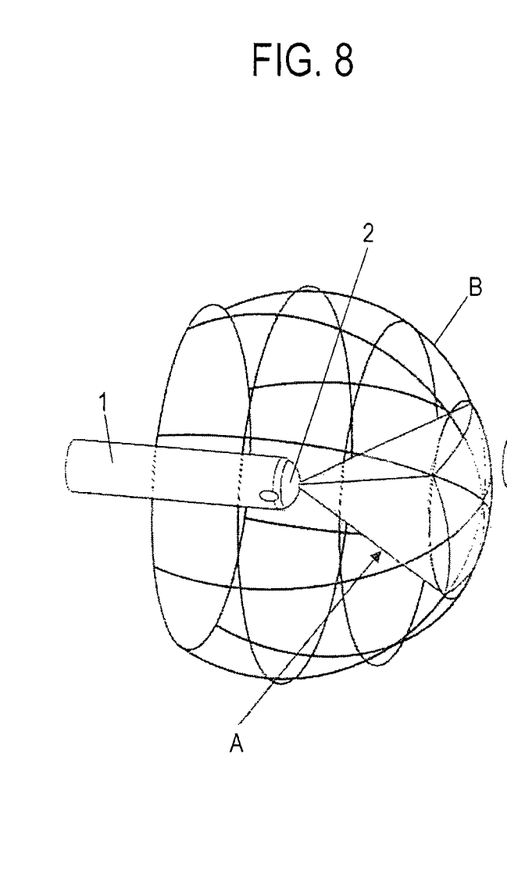
FIG. 8 shows a schematic perspective view of a distal portion of an endoscope with a zoomed axial image section of the field of view of the wide-angle lens.

FIG. 8 shows a situation with a zoomed axial image section A from the field of view B of the wide-angle lens 2. In this image section A of FIG. 8, the scene occurring distally in front of the endoscope (in the distal direction) can be recognized. Magnifying the center of the image results in an image from the common perspective and in a larger image scale. Such an image can, for example, be used upon introducing or moving forward the endoscope head 1.

Figure 9:
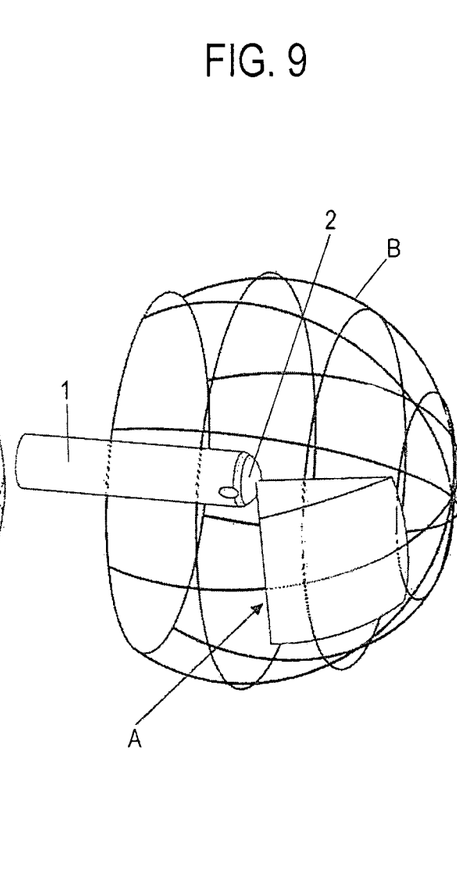
FIG. 9 shows a schematic perspective view of a distal portion of an endoscope with a zoomed image section of the field of view of the wide-angle lens, the image section resulting in the forward and lateral direction.

FIG. 9 shows a situation with a zoomed image section A from the field of view B of the wide-angle lens 2, the image section resulting in the forward and lateral direction. This image section is displaced within the total view such that a common image is formed, in which the bulged image geometry resulting due to the fisheye wide-angle is continuously equalized. Such an image can be used when the endoscope is moved forward when a front side of a diverticulum or an intestinal fold, seen relative to the endoscope head 1, is to be viewed.

The image resulting in FIG. 9 can also show a working site of an instrument as it is explained below by using FIG. 12.

Figure 10:
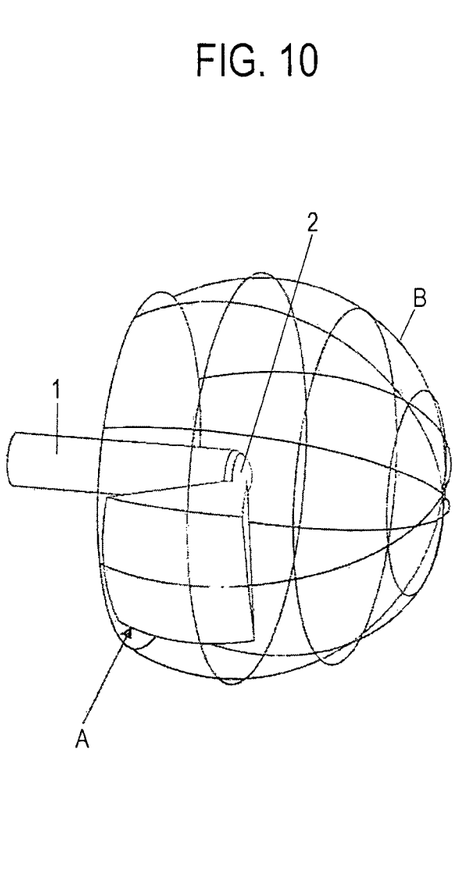
FIG. 10 shows a schematic perspective view of a distal portion of an endoscope with a zoomed image section of the field of view of the wide-angle lens, the image section resulting laterally at approximately 90°.

FIG. 10 shows a situation with a zoomed image section A from the field of view B of the wide-angle lens 2, the image section resulting laterally at approximately 90°. An equalized image from this perspective allows a natural side view. To obtain this image, it is neither necessary to move the camera to the side nor to displace the endoscope head 1. Such an image can be used when a back side, seen relative to the endoscope head 1, of the diverticulum or the intestinal fold, whose front side was examined in FIG. 9, is to be viewed.

Figure 11:
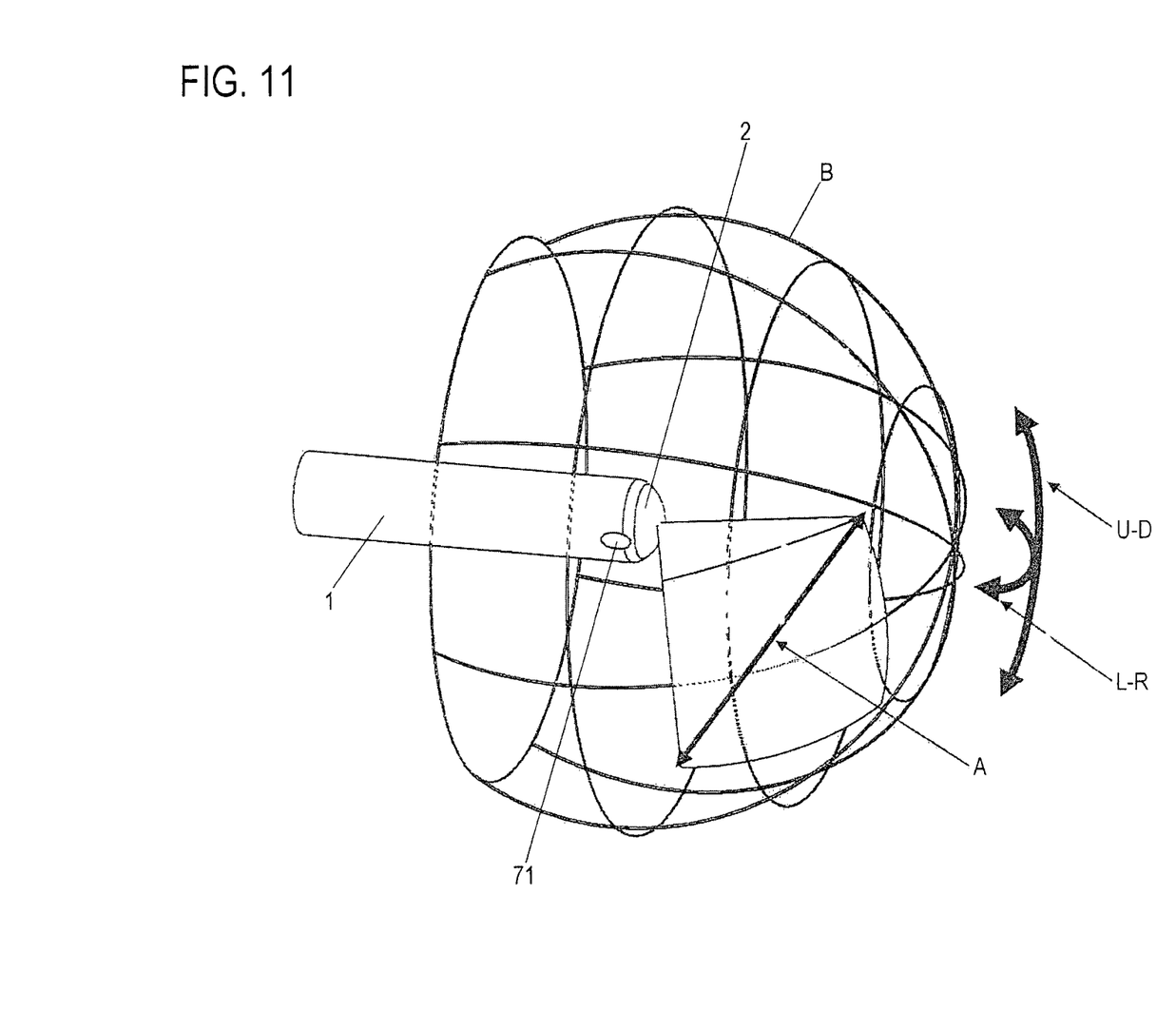
FIG. 11 shows a schematic perspective view of a distal portion of an endoscope with a zoomed image section of the field of view of the wide-angle lens, the image section resulting in the forward and lateral direction, wherein a displacement upon the selection of an image section is indicated.

FIG. 11 shows a situation with a zoomed image section A from the field of view B of the wide-angle lens 2. The image section A results in the forward and the lateral direction. Moreover, FIG. 11 shows how a selected image section A is equalized. A desired image section A is selected (here an image section A relative to the endoscope head 1 in the forward and the lateral direction). The selected image section A is displaced upward and downward, i.e. in the direction U-D, and to the left and the right, i.e. in the direction L-R. A combination of both directions U-D and L-R results in a diagonal displacement of the image section A. For the image section A, the magnification ratio can be selected, which is supposed to be indicated by the diagonal double arrow shown at the image section A.

Figure 12:
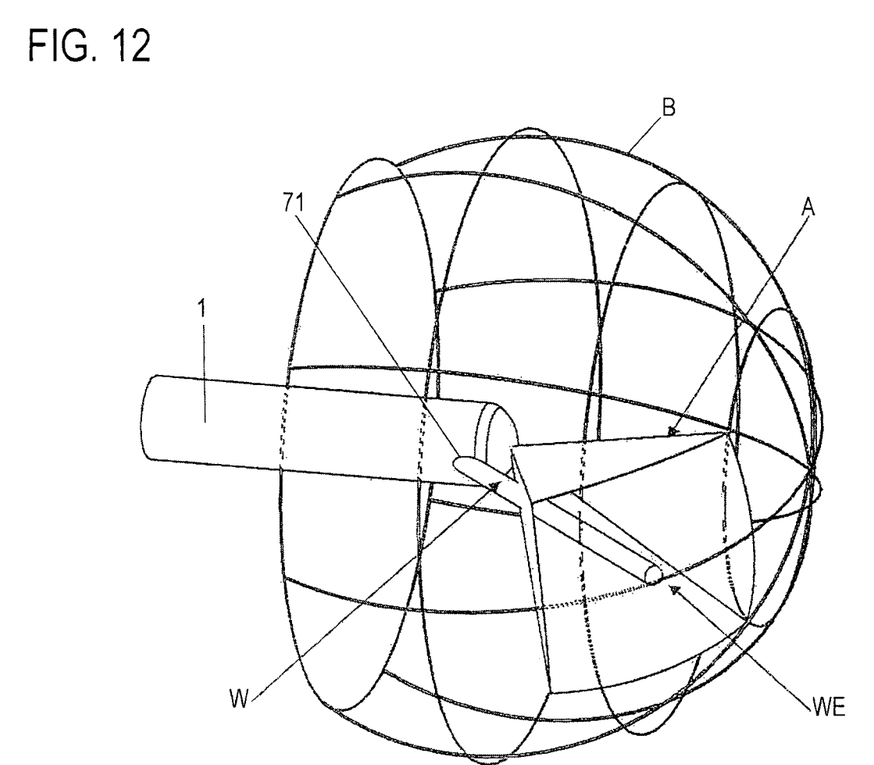
FIG. 12 shows a schematic perspective view of a distal portion of an endoscope with a zoomed image section as in FIG. 11, with an instrument emerging from a working channel.

FIG. 12 shows a situation with a zoomed image section A as in FIG. 11 with an instrument W emerging from a working channel 7. Here, the zoomed image section A is moved so far to the side that the instrument W obliquely emerging from the working channel 7 through the distal working channel opening 71 heads towards the image center of the image section A. Thus, the image section A can be selected such that exactly the tip WE of the instrument W can be viewed in the image center of the image section A.

Hence, in the invention, any sections of an image captured by the wide-angle lens 2 can be equalized by means of image processing and provided to the viewer.

Further Alternatives

Eight LEDs 3 are shown in the example of FIG. 1, but the invention is not restricted to a specific number of LEDs. Any number of LEDs can be used. Alternatively, an appropriate number of light guides (optical fibers) can be used as illumination means.

In the example of FIG. 1, the LEDs 3 are evenly distributed around the distal end surface of the wide-angle lens 2. Alternatively, the LEDs 3 can be randomly distributed around the distal end surface of the wide angle lens 2. Further LEDs 3 can be provided on the lateral circumferential surface of the endoscope head 1, proximally from the wide-angle lens 2.

The shape of the distal working channel opening 71 is not restricted. The distal working channel opening 71 can, for example, have a circular shape, a stadium shape, an elliptical shape, an oval shape or a rounded polygonal shape.

The distal portion of the working channel 7 and the distal portion of the water supply channel 8 can be guided in parallel to each other. Alternatively, they can extend in a non-parallel manner with respect to each other.

In the embodiment, the concentric annular depression 51 is formed on the distal end surface of the transparent cap 5. The LEDs 3 are arranged in the concentric annular depression 51 of the transparent cap 5. Between the LEDs 3, the concentric annular depression 51 of the transparent cap 5 is filled with a transparent material. Alternatively, the LEDs 3 can simply be covered by a lid which is pre-shaped in an appropriate form and has the same function as the transparent cap 5.

The invention can be advantageously used in a gastroscope, a colonoscope or a similar endoscope. The principle of the invention can also be applied in any other type of endoscope. Although the invention is particularly well suited for flexible endoscopes, it can also be applied in rigid endoscopes.

LIST OF REFERENCE SIGNS 1 endoscope head
2 wide-angle lens
3 illumination means, LED
4 channel for air/water
5 transparent cap
6 image sensor
7 working channel
8 water supply channel
21 foreign light protection
41 spray nozzle for lens cleaning
51 concentric annular depression
61 cable channel for image sensor
71 distal working channel opening
81 spray nozzle
A image section
B field of view of the wide-angle lens
W instrument
WE tip of the instrument

The invention claimed is:
1. An endoscope comprising:
an endoscope head,
a wide-angle lens on a distal end of the endoscope head, and
a working channel extending in the endoscope head,
wherein, proximally from the wide-angle lens, the working channel is bent laterally toward an outer circumference of the endoscope head,
wherein a distal working channel opening is formed on a lateral side of the endoscope head,
wherein the working channel includes a proximal working channel portion and a distal working channel end portion,
wherein the proximal working channel portion extends in parallel to a longitudinal axis of the endoscope, and
the distal working channel end portion is gently bent in a distal direction from the proximal working channel portion toward the distal working channel opening in a sloping manner;
wherein
the distal working channel end portion contacts the wide-angle lens, wherein on the distal end of the endoscope head, the wide-angle lens is completely or partially surrounded by a transparent region of the endoscope head,
wherein the transparent region of the endoscope head includes a transition edge where a distal side and the lateral side of the endoscope head meet, and
wherein at least a portion of the distal working channel opening is disposed in the transparent region.

2. The endoscope according to claim 1, wherein,
adjacent to the wide-angle lens, an illuminator is arranged on the distal end of the endoscope head, wherein the distal working channel opening opens proximally from the illuminator.

3. The endoscope according to claim 2, wherein
the illuminator surrounds a distal end region of the wide-angle lens in an annular manner or as a portion of a ring.

4. The endoscope according to claim 1, wherein,
adjacent to the wide-angle lens, an illuminator is arranged on the distal end of the endoscope head, wherein the distal working channel opening opens in the region of the illuminator.

5. The endoscope according to claim 1, wherein,
adjacent to the wide-angle lens, an illuminator is arranged on the distal end of the endoscope head, wherein the distal working channel opening opens in the region of the wide-angle lens.

6. The endoscope according to claim 1, wherein,
adjacent to the wide-angle lens, a sprayer for lens cleaning is arranged on the distal end of the endoscope head, wherein the distal working channel opening opens proximally from the sprayer.

7. The endoscope according to claim 1, wherein
the distal working channel end portion extends in the distal direction at an acute angle to a central axis of the endoscope head.

8. The endoscope according to claim 1, wherein
an opening of a water spray nozzle is provided adjacent to the distal working channel opening.

9. The endoscope according to claim 1, wherein,
proximally from the wide-angle lens, the distal working channel opening adjoins the wide-angle lens.

10. The endoscope according to claim 1, wherein,
on the lateral side of the endoscope head, the distal working channel opening extends into the wide-angle lens.

11. The endoscope according to claim 1, wherein
a field of view of the wide-angle lens is divided into several individual image sections, wherein from the several individual image sections, a specific image section is selectable.

12. The endoscope according to claim 11, wherein
the selected image section is digitally equalizable.

13. The endoscope according to claim 1, wherein
a viewing angle of the wide-angle lens is larger than 180°.

14. The endoscope according to claim 1, wherein
the endoscope is a flexible endoscope.

15. The endoscope according to claim 1, wherein
the endoscope is a video endoscope.

16. The endoscope according to claim 1, wherein at a distalmost surface of the distal end, a curvature of an outside surface of the wide-angle lens is continuous with a curvature of an outside surface the transparent region.

17. An endoscope comprising:
an endoscope head,
a wide-angle lens on a distal end of the endoscope head, and
a working channel extending in the endoscope head,
wherein, proximally from the wide-angle lens, the working channel is bent laterally toward an outer circumference of the endoscope head,
wherein a distal working channel opening is formed on a lateral side of the endoscope head,
wherein the working channel includes a proximal working channel portion and a distal working channel end portion,
wherein the proximal working channel portion extends in parallel to a longitudinal axis of the endoscope, and
the distal working channel end portion is gently bent in a distal direction from the proximal working channel portion toward the distal working channel opening in a sloping manner;
wherein
at least one portion of the distal working channel end portion extends into inside the wide-angle lens,
wherein on the distal end of the endoscope head, the wide-angle lens is completely or partially surrounded by a transparent region of the endoscope head,
wherein the transparent region of the endoscope head includes a transition edge where a distal side and the lateral side of the endoscope head meet, and
wherein at least a portion of the distal working channel opening is disposed in the transparent region.

18. The endoscope according to claim 17, wherein at a distalmost surface of the distal end, a curvature of an outside surface of the wide-angle lens is continuous with a curvature of an outside surface the transparent region.

19. An endoscope comprising:
an endoscope head,
a wide-angle lens on a distal end of the endoscope head, and
a working channel extending in the endoscope head,
wherein, proximally from the wide-angle lens, the working channel is bent laterally toward an outer circumference of the endoscope head,
wherein a distal working channel opening is formed on a lateral side of the endoscope head,
wherein the working channel includes a proximal working channel portion and a distal working channel end portion,
wherein the proximal working channel portion extends in parallel to a longitudinal axis of the endoscope, and
the distal working channel end portion is gently bent in a distal direction from the proximal working channel portion toward the distal working channel opening in a sloping manner;
wherein
the distal working channel end portion contacts the wide-angle lens,
wherein on a distal end side of the endoscope head, the wide-angle lens is surrounded by a transparent ring member, and
wherein at least a portion of the distal working channel opening is disposed in the transparent ring member.

20. The endoscope according to claim 19, wherein at a distalmost surface of the distal end, a curvature of an outside surface of the wide-angle lens is continuous with a curvature of an outside surface the transparent ring member.

21. An endoscope comprising:
an endoscope head,
a wide-angle lens on a distal end of the endoscope head, and
a working channel extending in the endoscope head, wherein, proximally from the wide-angle lens, the working channel is bent laterally toward an outer circumference of the endoscope head,
wherein a distal working channel opening is formed on a lateral side of the endoscope head,
wherein the working channel includes a proximal working channel portion and a distal working channel end portion,
wherein the proximal working channel portion extends in parallel to a longitudinal axis of the endoscope, and
the distal working channel end portion is gently bent in a distal direction from the proximal working channel portion toward the distal working channel opening in a sloping manner;
wherein
at least one portion of the distal working channel end portion extends inside the wide-angle lens,
wherein on a distal end side of the endoscope head, the wide-angle lens is surrounded by a transparent ring member, and
wherein at least a portion of the distal working channel opening is disposed in the transparent ring member.

22. The endoscope according to claim 21, wherein at a distalmost surface of the distal end, a curvature of an outside surface of the wide-angle lens is continuous with a curvature of an outside surface of the transparent ring member.

* * * * *